| United States Patent [19] | [11] | 4,110,163 |
|---|---|---|
| Hjortshoj et al. | [45] | Aug. 29, 1978 |

[54] BETA-GLUCANASE

[75] Inventors: Kirsten Hjortshoj, Vaerloese; Knud Aunstrup, Farum, both of Denmark

[73] Assignee: Novo Industri A/S, Bagsvaerd, Denmark

[21] Appl. No.: 730,014

[22] Filed: Oct. 6, 1976

Related U.S. Application Data

[63] Continuation of Ser. No. 443,324, Feb. 19, 1974, abandoned.

[30] Foreign Application Priority Data

Feb. 28, 1973 [GB] United Kingdom ............... 09844/73

[51] Int. Cl.$^2$ .......................... C07G 7/02; C12C 7/00; C12C 9/02
[52] U.S. Cl. ........................................ 195/62; 195/15; 195/31 R; 195/66 R; 426/12; 426/16; 426/29; 426/64
[58] Field of Search ................... 195/16, 33, 31 R, 62, 195/66 R, 15; 426/28, 29, 61, 64, 12, 16

[56] References Cited

U.S. PATENT DOCUMENTS

| 3,251,750 | 5/1966 | Tanaka et al. | 195/66 R |
| 3,591,457 | 7/1971 | Bender et al. | 195/66 R |
| 3,812,013 | 5/1974 | Bellamy et al. | 195/66 R |
| 3,880,742 | 4/1975 | James et al. | 195/66 R X |

OTHER PUBLICATIONS

Matsumura et al., Cellulolytic Enzymes Produced by *Aspergillus saitoi*, Chemical Abstracts, vol. 63, 1965 (4582h).

Basu et al., The Production of Cellulase by Fungi on Mixed Cellulosic Substrates, Canadian Journal of Microbiology, vol. 6, 1960 (pp. 265–281).

*Primary Examiner*—David M. Naff
*Attorney, Agent, or Firm*—Fidelman, Wolffe, & Waldron

[57] ABSTRACT

A beta-glucanase is prepared through the cultivation of *Aspergillus phoenicis* (Cda.) Thom or *Aspergillus saitoi var Kagoshimaensis*. This enzyme hydrolyzes the beta glucan of barley and can be employed to adjust the viscosity of wort, and beer, through incorporation of the enzyme in mash or beer.

5 Claims, No Drawings

BETA-GLUCANASE

This is a continuation of application Ser. No. 443,324, filed Feb. 19, 1974, now abandoned.

The invention relates to a process for the production of an enzyme preparation containing an enzyme which will hydrolyze the beta-glucan in barley and related glucans (a bata-glucanase). The invention also relates to the enzyme produced by the process as well as to the use of the enzyme preparation in the brewing arts to reduce the viscosity of wort and beer.

The conversion of barley to malt is a time consuming process requiring expensive equipment. A more economical use of the malt enzymes has been sought by using additional carbohydrates, such as maize, barley, rice or wheat. In Europe, barley is a common carbohydrate adjunct, but its use has caused problems in processing, particularly with regard to an increase in time required for filtration of the mash and the beer. This difficulty has also been found in poorly modified malts, i.e. malts containing insufficient enzymes. The prolonged separation times are due to the increased viscosity of the wort which is attributed to the presence of a gummy, high molecular weight polymer of D-glucose containing beta-1-3 and beta-1-4 glycosidic linkages, i.e. barley beta-glucan.

Additions of microbial protease and amylase have been used to maintain a satisfactory nitrogen level for yeast nutrition and to optimize the saccharification process both in mashing with carbohydrate-rich additives and poorly modified malts. These bacterial enzyme preparations, which normally are produced by *Bacillus subtilis*, do contain a proportion of endo-beta-glucanase which reduces the viscosity of the wort. However, the proportions of amylase, protease and beta-glucanase are governed by the ratios of enzymes formed by the bacteria so that treatment solely for viscosity reduction, when the malt amylolytic and proteolytic enzymes are adequate, is not possible. Moreover, the enzyme preparations containing endo-beta-glucanase, which have been used heretofore for viscosity reduction purposes, have a pH optimum which is considerably higher than the relatively low pH for fermenting beer.

The development of an enzyme preparation containing a high proportion of endo-beta-glucanase activity with relatively low pH optimum corresponding to the relatively low pH in the fermenting beer would have the advantage of allowing a more direct solution of viscosity problems and also permit more varied formulations of amylase, proteinase and beta-glucanase mixtures.

According to the invention, it has now been found that an endo-beta-glucanase preparation containing insignificant amounts of alpha-amylase and relatively little protease can be prepared by cultivating either *Aspergillus phoenicis* (Cda.) Thom (which for the sake of brevity in the following will be designated *Aspergillus phoenicis*) or *Aspergillus saitoi var Kagoshimaensis* under aerobic conditions in a suitable nutrient medium, followed by an isolation of the enzyme thus produced.

According to the invention, it has also been found that a beta-glucanase preparation prepared in this way may be added to mash or beer to adjust the viscosity of wort or beer. The new enzyme can be added to the wort or the beer independently or whether microbial amylase and/or microbial protease also has been added.

The enzyme of the present invention is different from bacterial glucanase. The two enzymes can be substituted to only a limited extent because of their pH characteristics.

For the purpose of beta-glucanase production *Aspergillus phoenicis* is, according to the invention, cultivated on a medium containing assimilable sources of carbon and nitrogen together with other essential nutrients, the medium being composed in accordance with the principles of the known art.

The species *Aspergillus phoenicis* is described by Raper and Fennell in the book "The Genus Aspergillus", Baltimore 1965, p. 307.

It must be noted that according to this definition, *Aspergillus saitoi var Kagoshimaensis* is identical to *Aspergillus phoenicis*.

In Table I the two strains used in the following examples are compared with the type strain as described in "The Genus Aspergillus".

|  | NRRL 5684 | CBS 137.52 | A. phoenicis (Cda.) Thom |
|---|---|---|---|
| Colonies on Czapek's solution agar diameter in cm after 7 days at 30° C | 6.5 | 7.0 | |
| 2 weeks at 24–26° C | | | 3.0 – 4.5 |
| colour reverse of colonies | dark brown colourless | dark brown colourless | dark brown white to slightly gray |
| *Sclerotia* | white, globose | white, globose | produced in some strains. white globose commonly 1-2 |
| diameter, mm | 1–2 | 1–2 | |
| *Conidial* heads form | loosely columnar | loosely columnar | globose when young, but splitting into few columns |
| colour | brown to black | brown to black | light tan to black |
| diameter, μ | ca. 400 | ca. 450 | 300–500 |
| *Conidiophores* colour | lightly coloured | lightly coloured | lightly coloured near the vesicle |
| length, mm | up to 3.0 | 1.5 – 2.5 | 1.0 – 2.5 |
| diameter, μ | 10–20 | 10–18 | 10–20 |
| walls | smooth | smooth | smooth |
| thickness, μ | 1.5 – 2 | 1.5 – 2 | 1–2 |
| *Vesicles* form | globose | globose | globose |
| diameter, μ | 50–80 | 40–80 | 45–65, occasionally up to 80–85 |
| Primary *sterigmata* colour | brownish | brownish | brownish |
| size, μ | 20–40 by 5–8 | 20–30 by 5–7 | 20–60 by 5.5 – 7.5 |
| Secondary *sterigmata* size, μ | 6–9 by 2–3 | 6–12 by 2–4 | 6.5 – 11.0 by 3.0 – 3.5 |
| *Conidia* form | globose, conspicuously roughened | globose, conspicuously roughened | globose, from almost smooth to irregularly roughened |
| diameter, μ | 2.5 – 3.5 | 3.0 – 3.5 | 3.0 – 3.5, but up to 4.0 |

The temperature at which the cultivation is usually carried out is within the range normally employed for the cultivation of *Aspergillus phoenicis*, preferably 25° to 25° C. As the cultivation has to be carried out under aerobic conditions, it is necessary to make use of artificial aeration, when growing the fungus in submerged culture with amounts of air used in conventional cultivation processes. Thus, it is preferred to use an aeration rate of 0.5 to 1.5 volumes of air per volume of liquid per minute in a closed fermentation vessel.

During fermentation the enzyme activity in the broth is determined regularly by the methods described below. When no further increase in activity occurs, the fermentation is stopped. Fermentation time is usually between 3 and 15 days.

Liquid enzyme preparations may be prepared from the broth by removing coarse materials from the broth, e.g. by centrifugation or filtration. The preparation may then be concentrated by evaporation at low temperatures or by reverse osmosis. Finally, preservatives may be added to the broth.

Solid enzyme preparations can be made from the purified and/or concentrated broth by precipitation with salts, such as sodium sulphate or ammonium sulphate, or with water-miscible solvents, such as ethanol or acetone; water can be removed from the preparation by suitable drying methods, such as spray- or freeze-drying.

The invention is further illustrated in the following examples, where the glucanase activity is determined as described below.

Beta-glucan was prepared from an aqueous extract of milled barley which was destarched by a bacterial alpha-amylase preparation containing no beta-glucanase activity. The destarched extract was then precipitated with acetone, redissolved in water, and reprecipitated with 30% ammonium sulphate. The preparation was then exhaustively dialysed against distilled water and freeze-dried to form a white fibrous product.

0.3% reducing sugar groups could be detected in the beta-glucan as prepared, when analyzed by the Nelson-Somogyi method (J. Biol. Chem. 153 375 1944). After hydrolysis with strong acid, by the Minnesota method, 95% sugar could be detected (Whistler, Wolfram, Methods in Carbohydrate Chemistry, Vol. 1962, p. 388).

A 2% solution of the beta-glucan has a viscosity of about 10 centipoises in 0.5% $KH_2PO_4$ adjusted to pH 7 at 30.0° C. This viscosity was unaltered by the addition of bacterial alpha-amylase, and fungal pentosanase, so indicating that no high molecular weight alpha-glucans or pentosans were present in the preparation.

The reaction with enzyme was performed in a 0.5% betaglucan solution buffered at pH 5.5, reaction time 30 minutes, temperature 30° C. A unit of activity was defined as the amount of enzyme which liberated reducing groups equivalent to 1 $\mu$ mol glucose per minute as determined by the Nelson-Somogyi method.

The new enzyme has a pH optimum at 5.5, which appears from the following table.

| pH | 2.0 | 3.0 | 4.0 | 5.5 | 6.0 | 7.0 |
|---|---|---|---|---|---|---|
| activity, % | 30 | 57 | 99 | 100 | 77 | 21 |

The stability of the new enzyme has been investigated under various circumstances, viz.:

After 24 hours at 30° C the residual activity is more than 95% of the original activity at pH values between 3.5 and 7.0.

After 1 hour at 50° C the residual activity is more than 85% of the original activity at pH values between 4.0 and 6.0.

After 1 hour at 60° C the residual activity is more than 37% of the original activity at pH values between 4.5 and 6.0.

Due to the above mentioned low pH optimum, this enzyme is specially suited for treatment of the beer during fermentation, because the beer during fermentation has a relatively low pH, between around 4.0 and 5.3.

EXAMPLE I

In 500 ml Erlenmeyer flasks is prepared a 100 ml solution of a medium of the composition (in g per liter):

| | |
|---|---|
| ground barley | 100 |
| potato starch | 40 |
| soybean meal | 30 |
| $Na_2SO_4$ | 1 |
| $CaCO_3$ | 5 |
| $KH_2PO_4$ | 3 |
| tap water to volume | |

The flasks are sterilized by autoclaving for 45 minutes at 120° C. After cooling to room temperature they are inoculated with spores of *Aspergillus phoenicis* NRRL 5684.

The inoculated flasks were incubated at 30° C on a rotary shaking table. After 6 and 12 days, the beta-glucanase activity was determined on a filtrate of the culture liquid. The result was:

6 days' incubation: 13.5 units per ml
12 days' incubation: 21.4 units per ml

EXAMPLE II

An experiment was performed exactly as described in Example I, except that the flasks were inoculated with spores of *Aspergillus saitoi var Kagoshimaensis* (CBS 137.52, ATCC 11363, QM 8162).
The result was:

6 days' incubation: 11.7 units per ml
12 days' incubation: 25.4 units per ml

EXAMPLE III

An experiment was performed as described in Example I, except that the flasks were inoculated with spores from six different strains of *Aspergillus phoenicis* obtained from the culture collection Centraalbureau voor Schimmelcultures in Baarn, Holland. The maximum activity obtained with these strains were:

| | |
|---|---|
| CBS 118.36 | 4.4 units per ml |
| CBS 114.37 | 17.2 units per ml |
| CBS 139.48 | 5.8 units per ml |
| CBS 136.52 | 21.5 units per ml |
| CBS 137.54 | 11.8 units per ml |
| CBS 107.55 | 9.3 units per ml |

EXAMPLE IV

A seed culture is prepared with 200 ml culture liquid as in Example I by incubating at 30° C on a rotary shaking table for 48 hours. The entire volume comprising 200 ml is transferred to a 10 liters fermentation tank containing a substrate of the following composition (in g per liter):

| | |
|---|---|
| ground barley | 80 |
| soybean meal | 50 |
| sucrose | 40 |
| $KH_2PO_4$ | 2.5 |
| tap water to volume | |

Air is supplied at 1 v/v/minute. The temperature is kept at 30° C, and the impeller is run at 800 rpm. The pH is maintained above 3.0 by supplying 1 M NaOH. After 120 hours' fermentation the activity was 33.0 units per ml.

EXAMPLE V

The ability of the enzyme according to the invention to reduce wort viscosity was demonstrated in the following way:

50 g milled barley was suspended in 200 ml water and bacterial amylase was added (0.2 g BANL 120, NOVO, heat treated to remove beta-glucanase). The mash was heated after the following programme: 1 hour at 50° C, 1 hour at 63° C, 30 minutes at 76° C.

Thereupon a wort was prepared by centrifugation, diluted to 10° balling, and pH was adjusted to 5.0. To the wort was added beta-glucanase prepared according to Example I and the wort was incubated for 120 minutes at 30° C, whereupon the viscosity was determined using a Brookfield viscosimeter.

| Beta-glucanase addition units per g barley | Viscosity cp |
| --- | --- |
| 0 | 1.85 |
| 0.07 | 1.67 |
| 0.14 | 1.58 |
| 0.35 | 1.44 |
| 0.70 | 1.36 |
| 1.40 | 1.28 |

What is claimed:

1. A process for the production of an endo-beta-glucanase preparation, which will hydrolyze the beta-glucan in barley and related glucans, which comprises cultivating *Aspergillus phoenicis* at between 25° and 30° C in a submerged culture in a nutrient medium containing assimilable sources of carbon and nitrogen together with other essential nutrients under aerobic conditions, thereafter recovering endo-beta-glucanase from the broth.

2. A process as claimed in claim 1, wherein the aeration rate is between 0.5 and 1.5 volume of air per volume of culture liquid per minute.

3. A process as claimed in claim 1 wherein the fermentation is stopped after a fermentation time between 3 and 15 days.

4. A process as claimed in claim 1 wherein the recovery of the enzyme is carried out by precipitating the enzyme from the broth, then drying the precipitated enzyme.

5. An endo-beta-glucanase preparation prepared by the process of claim 1.

* * * * *